(12) United States Patent
Suzuki et al.

(10) Patent No.: US 10,874,357 B2
(45) Date of Patent: Dec. 29, 2020

(54) EYE MOVEMENT MEASURING DEVICE AND EYE MOVEMENT ANALYSIS SYSTEM

(71) Applicants: TOKAI OPTICAL CO., LTD., Aichi (JP); CHUBU UNIVERSITY EDUCATIONAL FOUNDATION, Aichi (JP); NAC IMAGE TECHNOLOGY INC., Tokyo (JP); KABUSHIKI KAISHA TOKAI RIKA DENKI SEISAKUSHO, Aichi (JP)

(72) Inventors: Eiji Suzuki, Aichi (JP); Yutaka Hirata, Aichi (JP); Shogo Nakamura, Tokyo (JP); Shinichi Ueda, Aichi (JP); Masaya Yamamoto, Aichi (JP)

(73) Assignees: TOKAI OPTICAL CO., LTD., Aichi (JP); CHUBU UNIVERSITY EDUCATIONAL FOUNDATION, Aichi (JP); NAC IMAGE TECHNOLOGY INC., Tokyo (JP); KABUSHIKI KAISHA TOKAI TIKA DENKI SEISA KUSHO, Aichi (JP)

(*) Notice: Subject to any disclaimer, the term of this patent is extended or adjusted under 35 U.S.C. 154(b) by 0 days.

(21) Appl. No.: 16/376,363

(22) Filed: Apr. 5, 2019

(65) Prior Publication Data

US 2019/0231279 A1 Aug. 1, 2019

Related U.S. Application Data

(63) Continuation of application No. PCT/JP2017/036672, filed on Oct. 10, 2017.

(30) Foreign Application Priority Data

Oct. 11, 2016 (JP) .................................. 2016-200411

(51) Int. Cl.
*A61B 5/00* (2006.01)
*H04N 5/225* (2006.01)
(Continued)

(52) U.S. Cl.
CPC .............. *A61B 5/741* (2013.01); *A61B 3/113* (2013.01); *A61B 5/163* (2017.08); *A61B 5/165* (2013.01);
(Continued)

(58) Field of Classification Search
CPC ........... A61B 3/113; A61B 3/163; A61B 5/18; A61B 5/163; G02B 27/0172; G02B 2027/0178; G06F 3/013
See application file for complete search history.

(56) References Cited

U.S. PATENT DOCUMENTS 3,588,216 A * 6/1971 Bloom .............. B29D 11/00634
359/352
4,034,401 A * 7/1977 Mann ...................... F41G 3/225
348/115
(Continued)

FOREIGN PATENT DOCUMENTS

| JP | 2014-079374 A | 5/2014 |
| JP | 2015-109984 A | 6/2015 |
| JP | 2016-51317 A | 4/2016 |

OTHER PUBLICATIONS

International Search Report for PCT/JP2017/036672, dated Dec. 5, 2017, Total of 3 pages.

*Primary Examiner* — David E Harvey
(74) *Attorney, Agent, or Firm* — Tracy M Heims; Apex Juris, Pllc.

(57) ABSTRACT

An eye movement measuring device for detecting an eyeball-state/movement including: an eyeball photographing device configured to take a photograph of an eyeball; and an eye movement detecting unit configured to detect eye move-
(Continued)

ment based on eyeball image as a photograph taken with the eyeball photographing device, the eyeball photographing device including an eyeball illuminating unit configured to illuminate an eyeball of a subject including a driver with illumination light, an eyeball image imaging unit configured to obtain eyeball image as a result of imaging the illuminated eyeball, and an arranging unit configured such that, when the eyeball photographing device is worn by the subject, the eyeball illuminating unit is arranged in a position where the eyeball can be irradiated with the illumination light, and the eyeball image imaging unit is arranged in a position where the eyeball image can be obtained as a result of the imaging.

17 Claims, 3 Drawing Sheets

(51) Int. Cl.
| | |
|---|---|
| *G08B 7/06* | (2006.01) |
| *G08B 21/18* | (2006.01) |
| *B60W 50/16* | (2020.01) |
| *G02C 11/00* | (2006.01) |
| *A61B 5/16* | (2006.01) |
| *A61B 5/18* | (2006.01) |
| *A61B 3/113* | (2006.01) |
| *G02C 7/00* | (2006.01) |
| *G02C 7/14* | (2006.01) |
| *G06F 3/01* | (2006.01) |
| *G02C 7/10* | (2006.01) |
| *G02C 11/04* | (2006.01) |
| *G08G 1/16* | (2006.01) |
| *G06F 3/0346* | (2013.01) |
| *B60K 28/06* | (2006.01) |
| *B60W 50/14* | (2020.01) |

(52) U.S. Cl.
CPC .............. *A61B 5/18* (2013.01); *A61B 5/7455* (2013.01); *B60K 28/06* (2013.01); *B60W 50/16* (2013.01); *G02C 7/00* (2013.01); *G02C 7/10* (2013.01); *G02C 7/14* (2013.01); *G02C 11/00* (2013.01); *G02C 11/04* (2013.01); *G02C 11/10* (2013.01); *G06F 3/01* (2013.01); *G06F 3/0346* (2013.01); *G08B 7/06* (2013.01); *G08B 21/18* (2013.01); *G08G 1/16* (2013.01); *H04N 5/2253* (2013.01); *H04N 5/2256* (2013.01); *B60W 2050/143* (2013.01)

(56) References Cited

U.S. PATENT DOCUMENTS

| | | | |
|---|---|---|---|
| 9,658,453 B1* | 5/2017 | Kress | G02B 27/0172 |
| 2008/0030685 A1* | 2/2008 | Fergason | A61B 5/163 |
| | | | 351/210 |
| 2013/0066213 A1* | 3/2013 | Wellington | A61B 5/6814 |
| | | | 600/475 |
| 2016/0139265 A1* | 5/2016 | Yahav | H04N 5/23219 |
| | | | 356/51 |
| 2017/0332901 A1* | 11/2017 | Hwang | A61B 3/14 |

\* cited by examiner

EYE MOVEMENT MEASURING DEVICE AND EYE MOVEMENT ANALYSIS SYSTEM

CROSS REFERENCE TO RELATED APPLICATIONS

This is a continuation application of International Patent Application No. PCT/JP2017/036672 filed on Oct. 10, 2017 claiming priority upon Japanese Patent Application No. 2016-200411 filed on Oct. 11, 2016, of which full contents are incorporated herein by reference.

BACKGROUND OF THE INVENTION

Field of the Invention

The present invention relates to an eye movement measuring device to be worn by a driver or the like of a vehicle for measuring eye movement of the driver or the like, and to an eye movement analysis system for performing various analyses such as an analysis of states of consciousness of the driver or the like based on the eye movement obtained with the eye movement measuring device.

Description of the Background Art

There has been a need to develop a technique of monitoring states of a driver or the like of a vehicle in order to reduce accidents caused by human errors of the driver or the like, etc. The eye movement of the driver or the like has been known to reflect the states of consciousness of the driver or the like such as a degree of arousal and a degree of carelessness, and therefore, there have been attempts to sense the states of the driver or the like by measuring the eye movement. As a device for measuring such eye movement, a device that irradiates a face of a subject, including an eyeball, with sensing light so as to image an eye, has been proposed (see, for example, Patent Document 1).

PRIOR ART DOCUMENT

Patent Document

Patent Document 1: Japanese Patent Application Publication No. 2016-051317

Problem to be Solved

Conventionally, the imaging device that has been proposed is used in, for example, a state in which the imaging device is arranged in a vehicle in advance so as to face an eyeball. Thus, there was a risk in that stable imaging may not be performed since the positional relation between the imaging device and the eyeball may change when the driver or the like moves his/her head, and the eyeball may get out of the visual field of the imaging device. In addition, there was a risk in that ambient light may enter the imaging device, hindering obtainment of a clear image.

A goggle-type imaging device using a half mirror can maintain the positional relation between the imaging device and an eyeball at a predetermined relation. However, this would make the configuration thereof complicated and large in size, and there also is a risk in that ambient light may enter the imaging device, hindering obtainment of a clear image, as in the case of the aforementioned imaging device.

SUMMARY OF THE INVENTION

In view of the above-described problems, there is provided the present invention whose objective is to achieve: an eye movement measuring device having a structure that is so compact as to be easily attachable/detachable for the driver or the like and is capable of reducing the effect of ambient light so as to measure the eye movement with a high degree of precision; and an eye movement analysis system for performing various analyses such as analysis of the state of consciousness of the driver or the like based on the eye movement obtained with the eye movement measuring device.

Means for Solving Problems

As a first aspect of the present invention, there is adopted a technical means: an eye movement measuring device for detecting a state and a movement of an eyeball, the device comprising: an eyeball photographing device configured to take a photograph of an eyeball; and an eye movement detecting unit configured to detect eye movement based on eyeball image as a photograph taken with the eyeball photographing device, wherein the eyeball photographing device comprises an eyeball illuminating unit configured to illuminate an eyeball of a subject, who includes a driver, with illumination light, an eyeball image imaging unit configured to obtain eyeball image as a result of imaging the eyeball illuminated by the eyeball illuminating unit, and an arranging unit configured such that, when the eyeball photographing device is worn by the subject, the eyeball illuminating unit is arranged in a position where the eyeball can be irradiated with the illumination light, and the eyeball image imaging unit is arranged in a position where the eyeball image can be obtained as a result of imaging the eyeball.

According to the first aspect of the present invention, the eyeball photographing device can irradiate the eyeball with the illumination light through the use of the eyeball illuminating unit, and can obtain the eyeball image as a result of imaging the eyeball illuminated by the eyeball illuminating unit through the use of the eyeball image imaging unit. The eye movement can be detected by the eye movement detecting unit based on the eyeball image as a photograph taken with the eyeball photographing device. By the arranging unit, the eyeball illuminating unit and the eyeball image imaging unit can be easily arranged in predetermined positions. In such a manner, it is possible to achieve the eye movement measuring device having a structure that is so compact as to be easily attachable/detachable for the driver or the like and is capable of reducing the effect of ambient light so as to measure the eye movement under a stable condition. The "driver or the like" indicates a driver of a vehicle, an operator of a device, or the like.

As a second aspect of the present invention in the first aspect of the eye movement measuring device, there is adopted a technical means wherein said device includes an eye movement measuring device for measuring a state and a movement of an eyeball of the subject wearing eyeglasses, and the eyeball illuminating unit and the eyeball image imaging unit are arranged by the arranging unit with respect to the worn eyeglasses.

According to the second aspect of the present invention, the eye movement can be measured for the driver or the like allowed to wear the eyeglasses in regular use.

As a third aspect of the present invention in the first or second aspect of the eye movement measuring device, there is adopted a technical means further comprising a reflecting unit configured to allow visible light to pass therethrough, while reflect the illumination light of the eyeball illuminating unit so as to guide the reflected illumination light toward the eyeball, and reflect eyeball image, to be captured by the eyeball image imaging unit, toward the eyeball image imaging unit, wherein, the arranging unit is further configured such that, with respect to the reflecting unit, the eyeball illuminating unit is arranged in a position where the eyeball can be irradiated with the reflected illumination light, and the eyeball image imaging unit is arranged in a position where the eyeball image can be obtained as a result of capturing the reflected eyeball image, and wherein the eyeball image imaging unit obtains the eyeball image of the eyeball illuminated by the eyeball illuminating unit, as a result of capturing the reflected eyeball image of the eyeball irradiated with the reflected illumination light, through the reflecting unit, from a back or a side with respect to the eyeball.

According to the third aspect of the present invention, the reflecting unit can reflect invisible light emitted by the eyeball illuminating unit so as to guide the reflected invisible light toward the eyeball, and also, can reflect the eyeball image of the eyeball irradiated with the reflected invisible light. The eyeball image imaging unit can obtain the eyeball image of the eyeball illuminated by the eyeball illuminating unit, as a result of capturing the returned eyeball image, through the reflecting unit, from a back or a side with respect to the eyeball. In such a manner, the eyeball photographing device can be configured as a more compact structure. In addition, it is possible to achieve the eye movement measuring device capable of further reducing the influence of ambient light so as to measure the eye movement with a high degree of precision. The "a back or a side with respect to the eyeball" indicates a positional relation based on the eyeball surface shown on the face of the driver or the like.

As a fourth aspect of the present invention in any one of the first to third aspects of the eye movement measuring device, there is adopted a technical means wherein the arranging unit includes overglasses.

As a fifth aspect of the present invention in any one of the first to third aspects of the eye movement measuring device, there is adopted a technical means wherein the arranging unit includes clip-on glasses.

According to the fourth and fifth aspects of the present invention, overglasses and clip-on glasses can be suitably applied to the arranging unit.

As a sixth aspect of the present invention in any one of the first to fifth aspects of the eye movement measuring device, there is adopted a technical means wherein the illumination light emitted by the eyeball illuminating unit includes near-infrared light as invisible light.

According to the sixth aspect of the present invention, near-infrared light, as invisible light enabling imaging at night-time, can be employed for the illumination light.

As a seventh aspect of the present invention in any one of the first to fourth aspects of the eye movement measuring device, there is adopted a technical means wherein the illumination light emitted by the eyeball illuminating unit includes ultraviolet light as invisible light.

According to the seventh aspect of the present invention, ultraviolet light as invisible light can be employed for the illumination light, without any interference of lenses of general eyeglasses with low transmittance of ultraviolet rays and insusceptibility to ambient light.

As an eighth aspect of the present invention in the sixth aspect of the eye movement measuring device, there is adopted a technical means wherein the reflecting unit includes a reflecting film configured to selectively reflect near-infrared light.

According to the eighth aspect of the present invention, the reflecting unit can be a reflecting film selectively reflects near-infrared light.

As a ninth aspect of the present invention in the eighth aspect of the eye movement measuring device, there is adopted a technical means wherein a lens of any one of a group of: eyeglasses; overglasses; and clip-on glasses is made of material absorbing near-infrared rays.

According to the ninth aspect of the present invention, the lens absorbs near-infrared rays, and therefore, the influence of near-infrared light as a component of the ambient light can be reduced, and the eyeball image can be obtained as a result of imaging the eyeball with a high degree of precision.

As a tenth aspect of the present invention in any one of the first to ninth aspects of the eye movement measuring device, there is adopted a technical means wherein an irradiating direction of the illumination light from the eyeball illuminating unit and a visual field direction of the eyeball image imaging unit are substantially the same as each other.

According to the tenth aspect of the present invention, invisible light of sufficient illuminating intensity can be applied in the visual field direction of the eyeball image imaging unit, and therefore, irradiation efficiency for the eyeball irradiated with such an invisible light is improved, and as a result, a clear image can be obtained.

As an eleventh aspect of the present invention in any one of the first to tenth aspects of the eye movement measuring device, there is adopted a technical means wherein the eyeball image imaging unit comprises a filter configured to absorb or reflect at least a portion of ambient light in the visible light spectrum and selectively allow the illumination light emitted by the eyeball illuminating unit to pass therethrough.

According to the eleventh aspect of the present invention, the ambient light in the visible light spectrum entering the imaging unit can be decreased by the filter while the invisible light to be used for imaging can pass through the filter, and therefore, the influence of the ambient light can be reduced, and the eyeball can be obtained as a result of imaging the eyeball with a high degree of precision.

As a twelfth aspect of the present invention, there is adopted a technical means: an eye movement analysis system comprising: an eye movement measuring device in any one of the above-described first to eleventh aspects; and a human state sensing unit configured to sense a state including a consciousness state of a subject, who includes a driver, based on eye movement detected by the eye movement detecting unit.

According to the twelfth aspect of the present invention, the eye movement analysis system includes the eye movement measuring device and the human state sensing unit, and therefore, the state such as a consciousness state of the driver or the like can be sensed by the human state sensing unit based on the eye movement detected by the eye movement detecting unit.

As a thirteenth aspect of the present invention in the twelfth aspect of the eye movement analysis system, there is adopted a technical means wherein said system is used for the driver of a vehicle, and wherein the human state sensing unit senses the consciousness state including a degree of arousal and a degree of carelessness of the driver.

According to the thirteenth aspect of the present invention, the consciousness state such as a degree of arousal and a degree of carelessness of the driver, which would cause human errors in vehicle driving, can be analyzed by said eye movement analysis system.

As a fourteenth aspect of the present invention in the thirteenth aspect of the eye movement analysis system, there is adopted a technical means further comprising a warning unit configured to warn the driver with a warning including a voice and vibration, when the human state sensing unit determines that the consciousness state of the driver is a predetermined state.

According to the fourteenth aspect of the present invention, the warning unit can call for attention by issuing a warning when it is determined that the consciousness state of the driver is in a predetermined state, such as a consciousness state dangerous for vehicle driving.

BRIEF DESCRIPTIONS OF THE DRAWINGS

For more thorough understanding of the present invention and advantages thereof, the following descriptions should be read in conjunction with the accompanying drawings in which:

FIG. 2 depicts an explanatory view showing, in a schematic manner, the arrangement of: an eyeball illuminating unit; an eyeball image imaging unit; and a reflecting unit, with respect to the eyeball of a driver or the like.

DESCRIPTIONS OF EMBODIMENTS OF THE INVENTION

First Embodiment

Figure 1:
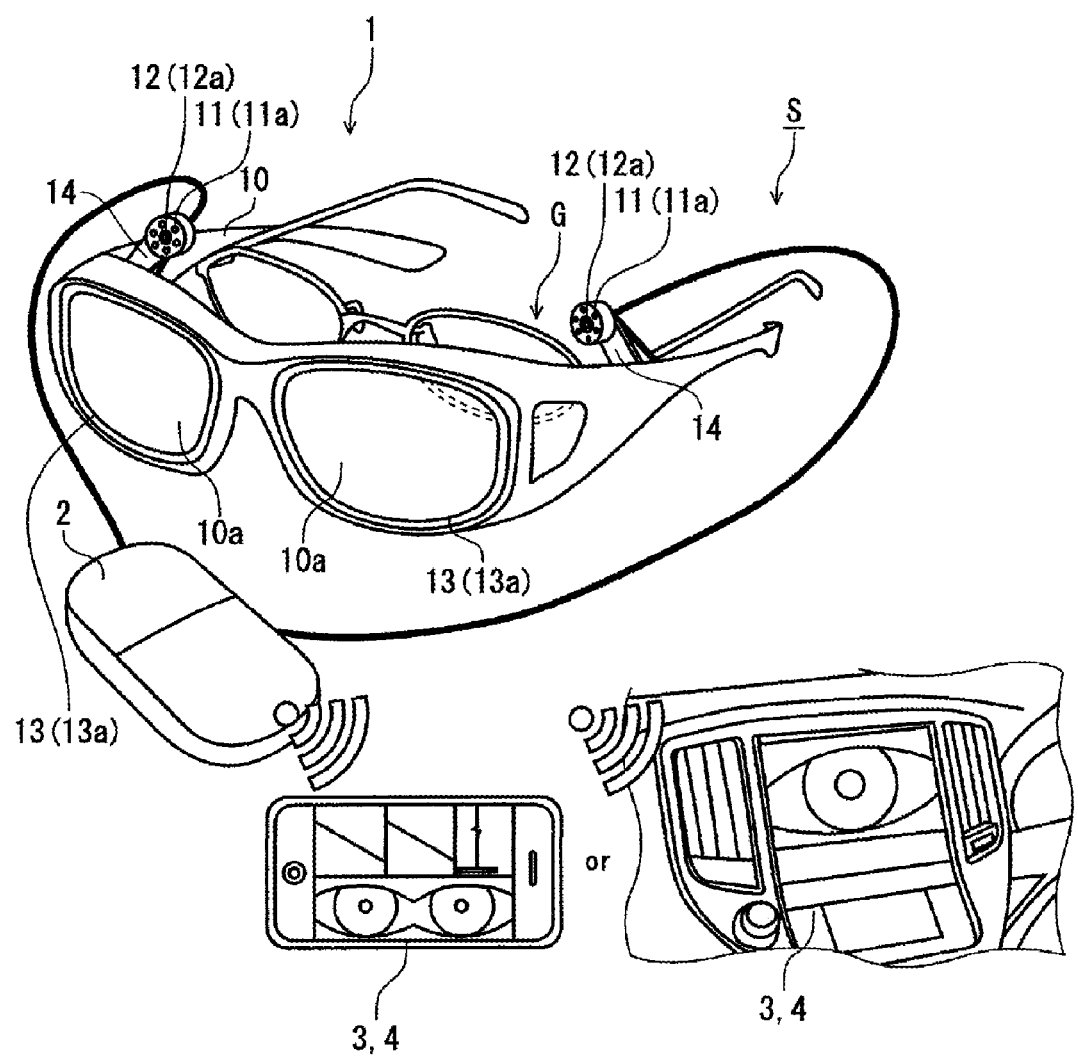
FIG. 1 depicts an explanatory view showing, in a schematic manner, the structure of: an eyeball photographing device; and an eye movement analysis system, as a first embodiment according to the present invention.

An eye movement analysis system S as an embodiment according to the present invention will be described with reference to the drawings. As shown in FIG. 1, the eye movement analysis system S includes an eyeball photographing device 1 that takes a photograph of an eyeball of a driver of a vehicle, an operator of a device, or the like (hereinafter, referred to as the driver or the like), an eye movement detecting unit 2 that detects eye movement based on an eyeball image photographed with the eyeball photographing device 1, and a human state sensing unit 3 that senses states such as states of consciousness of the driver or the like based on the eye movement detected by the eye movement detecting unit 2. In addition, a warning unit 4 that issues a warning based on the states of the driver or the like sensed by the human state sensing unit 3, is included. Here, the eyeball photographing device 1 and the eye movement detecting unit 2 form an eye movement measuring device.

The eyeball photographing device 1 as a first embodiment includes overglasses 10 that are mounted so as to cover eyeglasses G that are worn by the driver or the like, an eyeball illuminating unit 11 that illuminates an eyeball with invisible light, an eyeball image imaging unit 12 that images an eyeball image of the eyeball illuminated by the eyeball illuminating unit 11, a reflecting unit 13 that reflects the invisible light irradiated from the eyeball illuminating unit 11 to guide it to the eyeball, and reflects the eyeball image to be imaged to the eyeball image imaging unit 12, and an arranging unit that arranges the eyeball illuminating unit 11, the eyeball image imaging unit 12, and the reflecting unit 13 in predetermined positions with respect to the eyeglasses G.

Here, the arranging unit arranges the eyeball illuminating unit 11 with respect to the reflecting unit 13 in a position that enables the application of the invisible light to the eyeball, and arranges the eyeball image imaging unit 12 in a position that enables imaging of the eyeball image reflected by the reflecting unit 13.

In an embodiment, a near-infrared light LED 11a that emits near-infrared light, which is invisible light, as illumination light, is employed as the eyeball illuminating unit 11. Near-infrared light allows imaging also during the nighttime, and it can be suitably used. With the invisible light, the driver or the like does not perceive that the eyeball has been illuminated. Thus, since invisible light does not obstruct visual sense, ability to concentrate, and the like, it can be suitably used. With a fixing member 14, the near-infrared light LED 11a is attached to a temple 10b of the overglasses 10 in a position that does not block the visual field of the driver or the like, in a direction along which the near-infrared light can be applied toward the reflecting unit 13 provided in a lens part 10a of the overglasses 10. Here, the fixing member 14 includes an adjusting mechanism that adjusts orientations of the near-infrared light LED 11a and a near-infrared light camera 12a.

In an embodiment, the near-infrared light camera 12a is employed as the eyeball image imaging unit 12. The near-infrared light camera 12a is attached to the temple 10b of the overglasses 10 with the fixing member 14, together with the near-infrared light LED 11a. Here, an irradiating direction of the near-infrared light emitted from the near-infrared light LED 11a and a visual field direction of the near-infrared light camera 12a are substantially the same direction. With such arrangements, the invisible light having sufficient illuminating intensity can be applied in the visual field direction of the eyeball image imaging unit 12. Thus, irradiation efficiency of the invisible light to the eyeball improves, and a clear image can be obtained.

The near-infrared light camera 12a has an imaging cycle and precision that are required for the sensing of human states. For example, it is configured as a camera that can perform imaging with a frame rate of 200 frames per second and a resolution of 0.05°.

In an embodiment, the reflecting unit 13 is formed on the eyeball side surface of the lens part 10a of the overglasses 10, as a reflecting film 13a that transmits visible light in which the reflectivity of near-infrared light is selectively high. A known coating film that reflects near-infrared light, such as a coating film disclosed in Japanese Patent Application Publication No. 2015-148643, can be employed as the reflecting film 13a.

Figure 2:
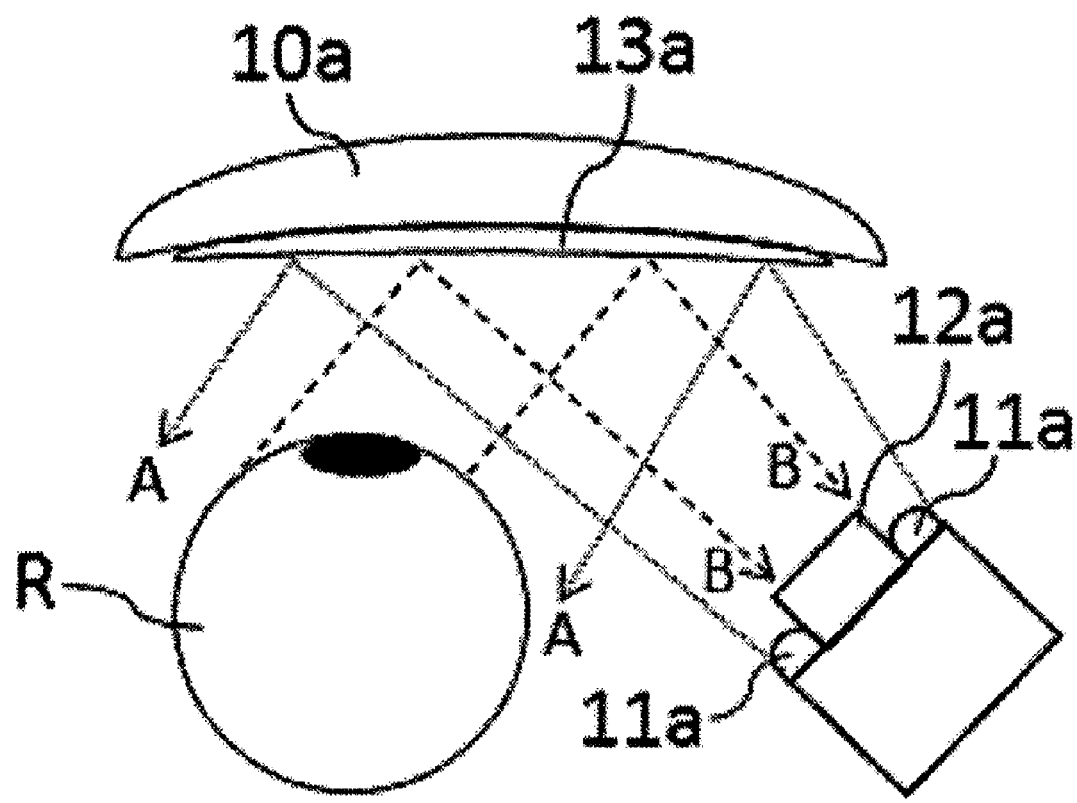

FIG. 2 shows arrangements of the near-infrared light LED 11a, the near-infrared light camera 12a, and the reflecting film 13a, with respect to a right eye R of the driver or the like. FIG. 2 schematically shows the arrangements when the eyeball photographing device 1 is seen from above the head of the driver or the like. For simplification, illustration of the eyeglasses G is omitted.

The near-infrared light LED 11a is arranged in a position that enables the irradiation of the near-infrared light as in a path A, to the eyeball, at least to the iris and the pupil, of the right eye R through the reflecting film 13a.

The near-infrared light applied to the right eye R enters into the near-infrared light camera 12a through the reflecting film 13a as in path B, to be imaged as an eyeball image.

In an embodiment, both the fixing member 14 which arranges the near-infrared light LED 11a and the near-infrared light camera 12a as well as the overglasses 10 which include the temple 10b where the fixing member 14 is attached and the lens 10a where the reflecting film 13a is arranged correspond to the arranging unit.

Since the positional relation between the overglasses 10 and the eyeglasses G is constant, in an embodiment, both the fixing member 14 which arranges the near-infrared light LED 11a and the near-infrared light camera 12a as well as the overglasses 10 which include the temple 10b where the fixing member 14 is attached and the lens 10a where the reflecting film 13a is arranged correspond to the arranging unit.

In this manner, in the eyeball photographing device 1 as a first embodiment, the near-infrared light LED 11a, the near-infrared light camera 12a, and the reflecting film 13a are arranged in the overglasses 10. Thus, even if the head of the driver or the like moves, the movement will be followed, and the positional relations with the eyeball will not change. In addition, the eyesight of the driver or the like will not be blocked.

Furthermore, since the eyeball is illuminated by the near-infrared light, which is invisible light, the driver or the like can perform vehicle driving, operation of a device, and the like, while looking the front carefully without being aware of the imaging of the eyeball.

The overglasses 10 can employ a configuration in which the lens 10a is formed of a lens that absorbs/blocks near-infrared light from the outside world, such as a lens into which copper ions are introduced. In this manner, it is possible to prevent the near-infrared light included in ambient light from being transmitted through the lens 10a, and entering into the near-infrared light camera 12a from the front side of the overglasses 10. Thus, the influence of the ambient light during the imaging of the eyeball can be reduced, and the eyeball can be imaged with high precision. In addition, since the influence of the ambient light can be reduced, irradiation intensity of the near-infrared light application to the eyeball can also be reduced.

The eye movement detecting unit 2 and the human state sensing unit 3 are formed of devices that include an arithmetic processing function such as computers and portable terminals such as smartphones. The eye movement detecting unit 2 and the human state sensing unit 3 can perform detection of eye movement based on an eyeball image photographed with the eyeball photographing device 1, and sensing of states such as the states of consciousness of the driver or the like based on the eye movement detected by the eye movement detecting unit 2, respectively, in accordance with programs recorded in said unit.

The eye movement detecting unit 2 and the human state sensing unit 3 can be formed as the same computer for arithmetic processing. Also, when the present system is mounted on a vehicle such as an automobile, for example, an engine control unit (ECU) can be shared as the computer for arithmetic processing.

The eye movement detecting unit 2 supplies power to the eyeball illuminating unit 11 and the eyeball image imaging unit 12, and performs control of each of them. Furthermore, the eye movement detecting unit 2 obtains an eyeball image from the eyeball image imaging unit 12 at predetermined time intervals, and sends the data to the human state sensing unit 3. In an embodiment, the eye movement detecting unit 2 includes a communication unit, and it sends out the data from the eye movement detecting unit 2 to the human state sensing unit 3 by radio communication.

In the eye movement detecting unit 2, the irradiation of the near-infrared light by the near-infrared light LED 11a may be performed by continuously lighting the near-infrared light LED 11a, or the irradiation timing may be controlled such that it is synchronized with the imaging cycle of the near-infrared light camera 12a.

States of an eyeball such as eye movement and changes in pupil diameter are closely related to the states of consciousness of the driver or the like. The human state sensing unit 3 senses the states such as the states of consciousness of the driver or the like based on the eye movement detected by the eye movement detecting unit 2. Processing such as image processing is performed on the imaged data of the eyeball to extract various parameters, and based on the values or changes of those parameters, the states of consciousness, such as a degree of arousal and a degree of carelessness, of the driver or the like can be sensed.

The human state sensing unit 3 is configured such that sensors, such as gyroscopes, that are required for various analyses can be connected thereto. Output signals from these sensors can be obtained for use in analyses.

With regard to the sensing of the states of consciousness of the driver or the like, for example, the degree of carelessness of the driver or the like can be sensed by detecting a convergence angle or divergence of both eyes.

In addition, a triaxial acceleration sensor that detects linear acceleration and a gyroscope that detects rotational angular velocity, for example, for detecting the linear acceleration and the rotational angular velocity caused in the head of the driver of the vehicle can be prepared as auxiliary device. By detecting vestibulo-ocular reflex (VOR), the degree of arousal of the driver such as a sign of drowsiness can be determined based on the vestibulo-ocular reflex. Here, since a parameter to be used in this analysis can be calculated only with the movement of either of the eyeballs, the near-infrared light LED 11a, the near-infrared light camera 12a, and the reflecting film 13a only need to be prepared for one eye.

Furthermore, for example, a visual line camera that is capable of detecting a visual line direction of the driver or the like may be prepared as an auxiliary device, and the states of consciousness of the driver or the like can be sensed by combining data of visual line behaviors with the change rate of the pupil diameter.

The warning unit 4 issues a warning based on the states of the driver or the like sensed by the human state sensing unit 3. For example, the warning unit 4 is configured to issue a warning sound or warning message when the human state sensing unit 3 determines that the driver or the like is feeling drowsy. Here, various modes can be employed as the ways of issuing the warning, such as connecting to an ECU to display the warning on a display of the vehicle, changing the air conditioning or the indoor lighting, and tightening the seat belt.

(Modification)

With regard to the driver or the like who does not use the eyeglasses G, the overglasses 10 can be used alone.

The near-infrared light camera 12a may be configured so as to include a filter that absorbs or reflects at least a portion of ambient light in a visible light region, and selectively transmits a near-infrared ray emitted by the near-infrared light LED 11a. For example, a resin plate to which a visible light absorbing-pigment or near-infrared ray transmitting-pigment is added, a visible light reflective coating by a dielectric multilayer, or the like can be employed. In this manner, since near-infrared light to be used for the imaging of the eyeball can be caused to selectively enter the near-infrared light camera 12a, the eyeball can be imaged with high precision, being hardly affected by the ambient light.

As an alternative to the reflecting film 13a, a similar configuration can be achieved by applying a sticker that selectively reflects near-infrared light on the lens of the eyeglasses G. Other than stickers, the lens Ga can be coated by spraying a liquid including a component that reflects near-infrared light.

Ultraviolet light can also be used as the invisible light. At this time, an ultraviolet light LED is used as the eyeball illuminating unit 11, an ultraviolet camera is used as the eyeball image imaging unit 12, and an ultraviolet light reflecting film is used as the reflecting unit 13. The lens 10a of the overglasses 10 and the lens of the eyeglasses G generally have low transmittance of ultraviolet light, and thus these are suitable due to being able to reduce the influence of ambient light during the imaging of the eyeball.

As illumination light by the eyeball illuminating unit 11, illumination light in the visible light region can also be used instead of the invisible light. At this time, in order to reduce the influence of the ambient light, the reflecting unit 13 is preferably configured so as to selectively reflect the wavelength region of the illumination light.

Second Embodiment

Figure 3:
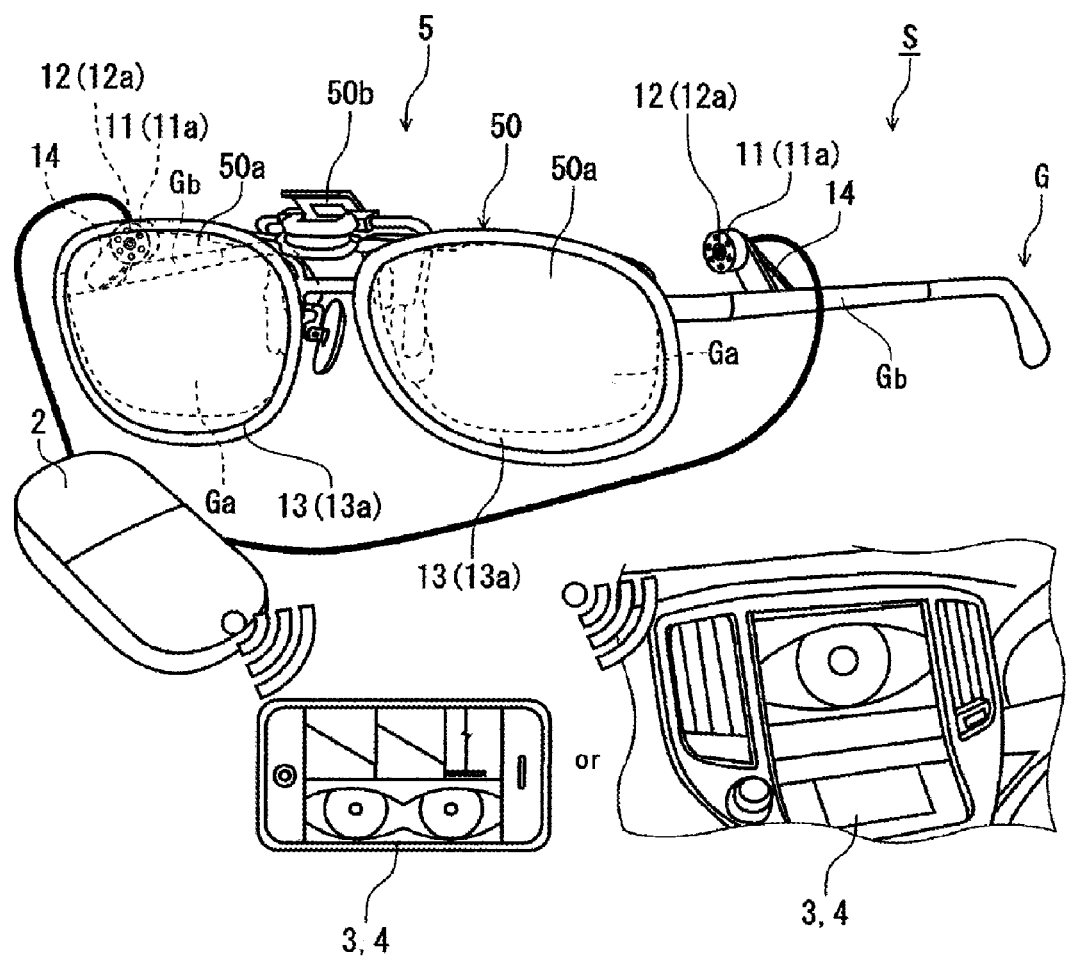
FIG. 3 depicts an explanatory view showing, in a schematic manner, the structure of: an eyeball photographing device; and an eye movement analysis system, as a second embodiment according to the present invention.

An eyeball photographing device 5 as a second embodiment according to the present invention is shown in FIG. 3. The eyeball photographing device 5 uses clip-on glasses 50 in which a lens 50a is mounted in front of the lens Ga of the eyeglasses G with a clip 50b, instead of the overglasses 10.

The configurations of the eyeball illuminating unit 11 and the eyeball image imaging unit 12 are the same as those of the eyeball photographing device 1 as a first embodiment according to the present invention. The eyeball illuminating unit 11 and the eyeball image imaging unit 12 are attached to the temple Gb of the eyeglasses G with the fixing member 14.

Here, the fixing member 14 is detachably formed in the temple Gb of the eyeglasses G with a known fixing means such as a clip, and it has a configuration that has an adjusting mechanism for adjusting the orientation of the near-infrared light camera 12a.

In an embodiment, the reflecting unit 13 is formed as the reflecting film 13a on the lens 50a of the clip-on glasses 50. Here, the reflecting film 13a can be formed in either the surface on the eyeball side or the surface on the opposite side of the eyeball, of the lens 50a.

As in the case of the lens 10a of the overglasses 10, a lens that absorbs/blocks near-infrared light from the outside world, such as a lens into which copper ions are introduced, can be employed as the configuration of the lens 50a of the clip-on glasses 50.

In an embodiment, the lens Ga of the eyeglasses G is preferably not provided with a function of absorbing or reflecting near-infrared light, so as to transmit near-infrared light for the imaging of the eyeball.

(Modification)

As an alternative to the reflecting film 13a formed in the lens 50a of the clip-on glasses 50, a similar configuration can be achieved by applying a sticker that selectively reflects near-infrared light on the lens Ga of the eyeglasses G, without mounting the clip-on glasses 50 on the eyeglasses G. In this manner, the driver or the like can use the eyeglasses G that have been regularly worn by himself/herself, as it is. Other than the sticker, the lens Ga can be coated by spraying a liquid including a component that reflects near-infrared light. In addition, as in the case of the lens 10a of the overglasses 10, a lens that absorbs/blocks near-infrared light from the outside world, such as a lens into which copper ions are introduced, can be employed as the configuration of the lens Ga of the eyeglasses G.

As in the case of a first embodiment according to the present invention, ultraviolet light can also be used as the invisible light. In addition, as illumination light by the eyeball illuminating unit 11, illumination light in the visible light region can be used instead of the invisible light.

Other Embodiments

A configuration in which the eyeball image imaging unit 12 is arranged in the front or on the side of the eyeball with the arranging unit, and the eyeball is directly imaged without using the reflecting unit 13, can also be employed. At this time, the eyeball photographing device 1 does not have to be provided with the reflecting unit 13.

The eye movement analysis system S can be used as a medical diagnostic device for diagnosing Parkinson's disease, autism, and schizophrenia, in which behavior characteristics are recognized in eye movement. In addition, it can be also used for sports vision evaluation or as a device for training.

Advantageous Effects Achieved By Embodiments

In the eye movement measuring device as embodiments according to the present invention, the eyeball photographing device 1 can illuminate an eyeball with invisible light by the eyeball illuminating unit 11, reflect the invisible light applied by the eyeball illuminating unit by the reflecting unit 13 to guide it to the eyeball, then reflecting an eyeball image, and image the eyeball image of the eyeball illuminated by the eyeball illuminating unit 11, by the eyeball image imaging unit 12 from the back or side of the eyeball. By the eye movement detecting unit 2, eye movement can be detected based on the eyeball image photographed with the eyeball photographing device. By the arranging unit, the eyeball illuminating unit 11, the eyeball image imaging unit 12, and the reflecting unit 13 can be easily arranged in predetermined positions. In this manner, it is possible to achieve the eye movement measuring device having a compact configuration that the driver or the like can put on and take off easily, while reducing the effect of ambient light, and can measure eye movement with high precision. In addition, eye movement can be measured while allowing the driver or the like to wear eyeglasses that have been regularly used by himself/herself. With the eye movement analysis system S, states such as states of consciousness of the driver or the like can be sensed by the human state sensing unit 3 based on the eye movement detected by the eye movement detecting unit 2. In addition, the states of consciousness, such as a degree of arousal and a degree of carelessness, of the driver, which become causes of human errors in vehicle driving, can be analyzed. When it is determined that the states of consciousness of the driver are in predetermined states, such as a state of consciousness that is dangerous for vehicle driving, the warning unit 4 can issue a warning to call for attention.

REFERENCE NUMERALS

1 Eyeball photographing device
2 Eye movement detecting unit
3 Human state sensing unit
4 Warning unit
5 Eyeball photographing device
10 Overglasses
10a Lens part 10b Temple
11 Eyeball illuminating unit
11a Near-infrared light LED
12 Eyeball image imaging unit
12a Near-infrared light camera
13 Reflecting unit
13a Reflecting film
14 Fixing member
50 Clip-on glasses
50a Lens
50b Clip
G Eyeglasses
Ga Lens
Gb Temple
S Eye movement analysis system

What is claimed is:

1. An eyeball movement measuring device for detecting a state and a movement of an eyeball, the device comprising:
an eyeball photographing device configured to take a photograph of an eyeball; and
an eyeball movement detecting unit configured to detect eyeball movement based on eyeball image as a photograph taken with the eyeball photographing device, wherein
the eyeball photographing device comprises
an eyeball illuminating unit configured to illuminate an eyeball of a subject, who includes a driver, with illumination light as invisible light,
an eyeball image imaging unit configured to obtain eyeball image as a result of imaging the eyeball illuminated by the eyeball illuminating unit, and
an arranging unit configured such that, when eyeglasses are worn by the subject,
the eyeball illuminating unit is arranged with respect to the worn eyeglasses in a position where the eyeball can be irradiated with the illumination light as invisible light, and
the eyeball image imaging unit is arranged with respect to the worn eyeglasses in a position where the eyeball image can be obtained as a result of imaging the eyeball, and wherein the eyeball image imaging unit comprises a filter configured to absorb or reflect at least a portion of ambient light as visible light passing through a lens arranged in front of the eyeball with respect to the worn eyeglasses, and selectively allow the illumination light as invisible light emitted by the eyeball illuminating unit to pass therethrough.

2. The eyeball movement measuring device according to claim 1, further comprising
a reflecting unit configured to
allow visible light to pass therethrough, while reflect the illumination light as invisible light of the eyeball illuminating unit so as to guide the reflected illumination light toward the eyeball, and
reflect eyeball image, to be captured by the eyeball image imaging unit, toward the eyeball image imaging unit, wherein,
the arranging unit is further configured such that, with respect to the reflecting unit,
the eyeball illuminating unit is arranged in a position where the eyeball can be irradiated with the reflected illumination light, and
the eyeball image imaging unit is arranged in a position where the eyeball image can be obtained as a result of capturing the reflected eyeball image, and wherein the eyeball image imaging unit obtains the eyeball image of the eyeball illuminated by the eyeball illuminating unit, as a result of capturing the reflected eyeball image of the eyeball irradiated with the reflected illumination light, through the reflecting unit, from a back or a side with respect to the eyeball.

3. The eyeball movement measuring device according to claim 1, wherein the arranging unit includes overglasses.

4. The eyeball movement measuring device according to claim 1, wherein the arranging unit includes clip-on glasses.

5. The eyeball movement measuring device according to claim 1, wherein the illumination light emitted by the eyeball illuminating unit includes near-infrared light as invisible light.

6. The eyeball movement measuring device according to claim 2, wherein the illumination light emitted by the eyeball illuminating unit includes near-infrared light as invisible light.

7. The eyeball movement measuring device according to claim 1, wherein the illumination light emitted by the eyeball illuminating unit includes ultraviolet light as invisible light.

8. The eyeball movement measuring device according to claim 2, wherein the illumination light emitted by the eyeball illuminating unit includes ultraviolet light as invisible light.

9. The eyeball movement measuring device according to claim 5, wherein the reflecting unit includes a reflecting film configured to selectively reflect near-infrared light.

10. The eyeball movement measuring device according to claim 6, wherein the reflecting unit includes a reflecting film configured to selectively reflect near-infrared light.

11. The eyeball movement measuring device according to claim 9, wherein a lens of any one of a group of: eyeglasses; overglasses; and clip-on glasses is made of material absorbing near-infrared rays.

12. The eyeball movement measuring device according to claim 10, wherein a lens of any one of a group of: eyeglasses; overglasses; and clip-on glasses is made of material absorbing near-infrared rays.

13. The eyeball movement measuring device according to claim 1, wherein an irradiating direction of the illumination light as invisible light from the eyeball illuminating unit and a visual field direction of the eyeball image imaging unit are substantially the same as each other.

14. An eyeball movement analysis system comprising:
an eyeball movement measuring device according to claim 1; and
a human state sensing unit configured to sense a state including a consciousness state of a subject, who includes a driver, based on eyeball movement detected by the eyeball movement detecting unit.

15. An eyeball movement analysis system comprising:
an eyeball movement measuring device according to claim 2; and
a human state sensing unit configured to sense a state including a consciousness state of a subject, who includes a driver, based on eyeball movement detected by the eyeball movement detecting unit.

16. The eyeball movement analysis system according to claim 14, wherein said system is used for the driver of a vehicle, and wherein the human state sensing unit senses the consciousness state including a degree of arousal and a degree of carelessness of the driver.

17. The eyeball movement analysis system according to claim 16, further comprising a warning unit configured to warn the driver with a warning including a voice and vibration, when the human state sensing unit determines that the consciousness state of the driver is a predetermined state.

* * * * *